(12) United States Patent
Eliaz et al.

(10) Patent No.: US 11,298,151 B2
(45) Date of Patent: Apr. 12, 2022

(54) DEVICE, SYSTEM AND METHOD FOR PERICARDIAL ACCESS

(71) Applicants: YISSUM RESEARCH DEVELOPMENT COMPANY OF THE HEBREW UNIVERSITY OF JERUSALEM LTD., Givat Ram (IL); HADASIT MEDICAL RESEARCH SERVICES AND DEVELOPMENT LTD., Jerusalem (IL)

(72) Inventors: Ran Eliaz, Tsur Hadasa (IL); Yonathan Avraham Demma, Jerusalem (IL); Ziv Menshes, Moshav Kirdon (IL); Or Hazan, Yehud (IL); Eva Abramov, Geva Binyamin-Adam (IL); Yaakov Nahmias, Rishon le Zion (IL); Amnon Buxboim, Tel Aviv (IL); Yoav Kan-Tor, Rehovot (IL); Yoav Mintz, Jerusalem (IL); Elchanan Fried, Jerusalem (IL)

(73) Assignees: YISSUM RESEARCH DEVELOPMENT COMPANY OF THE HEBREW UNIVERSITY OF JERUSALEM LTD., Jerusalem (IL); HADASIT MEDICAL RESEARCH SERVICES AND DEVELOPMENT LTD., Jerusalem (IL)

( * ) Notice: Subject to any disclaimer, the term of this patent is extended or adjusted under 35 U.S.C. 154(b) by 128 days.

(21) Appl. No.: 16/623,054

(22) PCT Filed: Jun. 17, 2018

(86) PCT No.: PCT/IL2018/050670
§ 371 (c)(1),
(2) Date: Dec. 16, 2019

(87) PCT Pub. No.: WO2018/235072
PCT Pub. Date: Dec. 27, 2018

(65) Prior Publication Data
US 2020/0163695 A1 May 28, 2020

Related U.S. Application Data

(60) Provisional application No. 62/521,465, filed on Jun. 18, 2017.

(51) Int. Cl.
*A61B 17/34* (2006.01)
*A61B 17/00* (2006.01)

(52) U.S. Cl.
CPC .... *A61B 17/3417* (2013.01); *A61B 17/00234* (2013.01); *A61B 17/3468* (2013.01); *A61B 17/3476* (2013.01); *A61B 2017/00026* (2013.01); *A61B 2017/00247* (2013.01); *A61B 2017/3458* (2013.01)

(58) Field of Classification Search
CPC .......... A61B 17/3417; A61B 17/00234; A61B 17/3468; A61B 17/3476;
(Continued)

(56) References Cited

U.S. PATENT DOCUMENTS

| 4,762,120 A | 8/1988 | Hussein |
| 5,591,191 A * | 1/1997 | Kieturakis ......... A61B 17/3417 604/164.01 |

(Continued)

FOREIGN PATENT DOCUMENTS

| EP | 3181071 A1 | 6/2017 |
| WO | 2015065898 A1 | 5/2015 |
| WO | WO-2015123700 A1 * | 8/2015 ........... A61B 1/3132 |

OTHER PUBLICATIONS

International Search Report and Written Opinion, International Application No. PCT/IL2018/050670, dated Sep. 17, 2018.

*Primary Examiner* — Tan-Uyen T Ho
*Assistant Examiner* — Bridget E. Rabaglia
(74) *Attorney, Agent, or Firm* — The Roy Gross Law Firm, LLC; Roy Gross (57) ABSTRACT

Device for accessing a pericardial space of a subject in need thereof, the device including a tubular member having an
(Continued)

atraumatic distal end and a thread formed on, and at least partially around, the outer surface of the tubular member, proximally to the distal end; wherein the thread is configured to cut, puncture and/or penetrate a pericardium.

13 Claims, 4 Drawing Sheets

(58) Field of Classification Search
CPC .......... A61B 2017/00026; A61B 2017/00247; A61B 2017/3458; A61B 2017/3454
USPC ....... 606/170, 171, 167, 162, 172, 178, 180, 606/185
See application file for complete search history.

(56) References Cited

U.S. PATENT DOCUMENTS

| | | |
|---|---|---|
| 5,630,805 A * | 5/1997 | Ternamian ......... A61B 17/3421 604/274 |
| 8,986,278 B2 | 3/2015 | Fung |
| 9,149,276 B2 | 10/2015 | Voss |
| 9,339,292 B2 | 5/2016 | Poore et al. |
| 9,572,581 B2 | 2/2017 | Vaughan |
| 2002/0058956 A1 * | 5/2002 | Honeycutt ..... A61B 17/320758 606/159 |
| 2002/0138091 A1 * | 9/2002 | Pflueger .......... A61B 17/32002 606/170 |
| 2011/0098531 A1 * | 4/2011 | To ..................... A61B 17/1671 600/114 |
| 2012/0116418 A1 * | 5/2012 | Belson ................. A61B 17/06 606/139 |
| 2012/0209306 A1 * | 8/2012 | Okoniewski ....... A61B 17/3476 606/185 |
| 2012/0238968 A1 | 9/2012 | Toy |
| 2013/0274782 A1 * | 10/2013 | Morgan ............ A61B 17/3494 606/185 |
| 2016/0235973 A1 | 8/2016 | Asleson |
| 2017/0119435 A1 | 5/2017 | Gross |
| 2017/0207467 A1 * | 7/2017 | Shelton, IV ........ H01M 6/5044 |

* cited by examiner

DEVICE, SYSTEM AND METHOD FOR PERICARDIAL ACCESS

RELATED APPLICATIONS

This application is a National Phase of PCT Patent Application No. PCT/IL2018/050670 having International filing date of Jun. 17, 2018 which claims the benefit of priority of U.S. Provisional Application No. 62/521,465 filed on Jun. 18, 2017 entitled DEVICE, SYSTEM AND METHOD FOR PERICARDIAL ACCESS. The contents of the above applications are all incorporated by reference as if fully set forth herein in their entirety.

TECHNICAL FIELD

The disclosure generally relates to devices, systems and methods for accessing an anatomical space of the body, in particular, in gaining access to the pericardial space through the pericardium.

BACKGROUND

Access to internal and external structures of the heart may be desirable for the treatment of cardiovascular disease. One way in which a heart may be accessed for device delivery is by an intravascular approach. However, intravascular access to the heart may not be applicable for delivery of larger devices, nor if external structures of the heart are targeted. In such circumstances, the heart may be accessed through an opening or puncture in the pericardium, which may provide direct access to the external (epicardial) surface of the heart. Accessing the heart via the pericardium is becoming a recognized access route to the heart and may be useful for a variety of applications, including device or drug delivery, left atrial appendage exclusion, ablation of fibrillating tissue, placement of leads, electrocardiographic imaging, and the like.

However, penetration of the pericardial space carries a great risk of harming the heart due to the fact that currently available techniques require puncturing the pericardium, which is only of a few millimeter thickness, by using a large needle directed straight towards the beating heart. The procedure thus requires a highly skilled and experienced specialist and even the smallest imprecisions may cause severe heart damage and often even have a fatal outcome.

There is thus an unmet need for a device allowing safe and easy access to the pericardial space.

SUMMARY OF THE INVENTION

The present disclosure relates to devices, systems and methods for gaining access to the pericardial space through the pericardium. The device generally includes a hollow, blunt ended screw, also referred to herein as a tubular member, having an atraumatic distal end and a thread on its outer surface. The atraumatic tip of the device is configured to engage or put pressure on the pericardium, but it does not cause its puncture. Once the atraumatic tip engages the pericardium, rotation of the tubular member causes the thread, positioned proximal to the atraumatic distal end, to cut, puncture and/or penetrate the pericardium essentially horizontally, thereby gaining access to the pericardial space. According to some embodiments, the thread may be sharp. According to some embodiments, the tread may operate as a horizontal cutter and or as a tangential scalpel. According to some embodiments, the thread includes a sharpened tip, while the remaining part of the thread is essentially blunt.

Advantageously, the atraumatic distal end and the essentially horizontally cutting screwing of the tread into the pericardium, ensures that sharp surfaces of the device do not point in the direction of the heart/myocardium, but rather the pericardium is penetrated essentially horizontally. Resultantly, the risk posed by a forward directed needle is largely avoided.

Additionally, by being disposed on an outer surface of the blunt ended tubular member, the thread may assist in the advancement of the tubular member toward the pericardium.

The essentially horizontal cutting, puncturing and/or penetration of the pericardium by the thread and/or tangential scalpel, disposed on the outer surface to the tubular member, allows advancing of the tubular member itself into the pericardial space. This may advantageously enable insertion of medical instruments and/or delivery of medicaments through the lumen of the tubular member into the pericardial space, either through the end opening if the tubular member is open ended or through a penetrable cap covering the end opening of the lumen, as essentially disclosed herein.

According to some embodiments, the device may further include at least one sensor, for example, on the atraumatic tip and/or on the thread, configured to detect penetration into the pericardial space. The sensor may be a bio-impedance sensor configured to detect a change in resistance, conductivity, current or other electrical parameter as a result of being immersed in the pericardial fluid. This advantageously enables controlling the operation (e.g. rotation and/or progression) of the device so as to further reduce the risk of damaging the heart.

According to some embodiments, there is provided a device for accessing a pericardial space of a subject in need thereof, the device comprising a tubular member having an atraumatic distal end and a wall having an outer surface and an inner surface forming a lumen; and a thread formed on, and at least partially around, said outer surface, proximal to said distal end; wherein said thread is configured to cut, puncture and/or penetrate a pericardium, when in use.

According to some embodiments, the thread includes at least two threads. According to some embodiments, the thread comprises a helical thread. According to some embodiments, the thread includes or is formed as a helical and/or horizontal blade. According to some embodiments, the thread includes a sharp distal tip. According to some embodiments, the thread surrounds the tubular member at least twice.

According to some embodiments, the atraumatic open ended distal end is configured to protect said subject's heart and/or myocardium from being damaged.

According to some embodiments, the thread is configured to cut, puncture and/or penetrate the pericardium at an essentially perpendicular and/or tangential angle relative to the longitudinal axis of the tubular member, when in use. According to some embodiments, the thread is configured to perform an essentially horizontal cut, puncture and/or penetration of the pericardium.

According to some embodiments, the thread is formed integrally with the tubular member.

According to some embodiments, the device includes at least one sensor configured to detect penetration of the device into the pericardial space. According to some embodiments, the sensor includes or is a bio-impedance sensor. According to some embodiments, the bio-impedance sensor is positioned on the distal end and/or on the thread. According to some embodiments, the at least one sensor further includes an additional sensor, configured to detect an approaching of the device to the subject's heart when in use and/or to monitor the subject's cardiac cycle. According to some embodiments, the additional sensor includes or is a pressure sensor.

According to some embodiments, the proximal end of the tubular member comprises an attachment mechanism configured to reversibly attach the tubular member to a handle. According to some embodiments, the proximal end of the tubular member comprises a securing element configured to ensure proper connection of the tubular member to the handle.

According to some embodiments, the tubular member has a length of 5-15 cm. According to some embodiments, the tubular member has an outer diameter in the range of 2-10 mm and an inner diameter in the range of 1-9 mm.

According to some embodiments, the tubular member is open ended, thereby enabling passing a medical instrument and/or medicament through the lumen into the pericardial space, when the device has penetrated into the pericardial space.

According to some embodiments, the tubular member includes a penetrable end-cap covering the lumen opening; wherein the penetrable end-cap is penetrable from within the lumen, such that a medical instrument and/or medicament passed through the lumen can enter the pericardial space.

According to some embodiments, there is provided a system for accessing a pericardial space of a subject in need thereof, the system comprising the herein disclosed device and a handle; wherein the handle includes a socket configured to receive the proximal end of the tubular member.

According to some embodiments, the handle includes a mechanism configured to rotate the device along its longitudinal axis when the proximal end is inserted into the socket. According to some embodiments, the handle includes a mechanism configured to allow longitudinal and/or horizontal movement of the tubular member.

According to some embodiments, the handle includes an open electrical circuit, the circuit configured to be closed by insertion of the tubular member into the socket, thereby facilitating supply of electrical power to the handle and/or the device.

According to some embodiments, the handle includes a processing unit configured to control rotation and/or movement of the tubular member based on one or more signals received from the at least one sensor of the tubular member.

According to some embodiments, the handle includes a method for accessing a pericardial space of a subject in need thereof, the method including: inserting a device into a chest cavity, wherein the device comprises a tubular member having an atraumatic distal end and a thread formed on, and at least partially around, an outer surface of said tubular member, proximal to said distal end; advancing the device to the pericardium until said atraumatic distal end reaches and/or presses against said pericardium; rotating said tubular member along its longitudinal axis, such that said thread cuts, punctures and/or penetrates said pericardium, thereby allowing said tubular member's distal end to enter said pericardial space.

According to some embodiments, the method further includes moving the tubular member along its longitudinal and/or axial axis concurrently with the rotating thereof, thereby screwing the thread through and/or into the pericardium.

According to some embodiments, the method further includes rotating the tubular member without advancement, thereby lifting and/or separating layers of the pericardium.

According to some embodiments, the method further includes generating a workspace by rotating the tubular member without advancement, thereby lifting and/or separating layers of the pericardium.

According to some embodiments, when the atraumatic distal end presses against the pericardium, the pericardial tissue folds around the thread.

According to some embodiments, the thread is configured to cut, puncture, and/or penetrate the pericardium essentially horizontally.

According to some embodiments, the method further includes obtaining a signal from one or more sensors configured to detect penetration of the device into the pericardial space. According to some embodiments, one or more sensors includes or is a bio-impedance sensor configured to detect a change in electrical resistance when the distal end and/or the thread penetrates into the pericardial space.

According to some embodiments, when a signal indicative of penetration into the pericardial space is obtained, the rotation and/or longitudinal movement of the tubular member is halted.

According to some embodiments, the method further includes inserting a medical instrument through the tubular member's lumen into the pericardial space.

According to some embodiments, the method further includes delivering a medicament through the tubular member's lumen to the pericardial space.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE FIGURES

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION OF THE INVENTION

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments, there is provided a device for accessing a pericardial space of a subject in need thereof, the device including a tubular member having an atraumatic distal end and a wall with an outer surface and an inner surface forming a lumen; and a thread formed on, and at least partially around, the outer surface of the tubular member, proximally to the distal end; wherein the thread is configured to cut, puncture and/or penetrate a pericardium, when in use.

According to some embodiments, the device may be suitable for minimally invasive procedures.

As used herein the term "tubular member" may refer to a hollow cylinder formed channel. According to some embodiments, the tubular member may be formed of a metal, a plastic, a bio compatible polymer or any other suitable rigid material. According to some embodiments, the tubular member may be formed from a material suitable for 3D printing. According to some embodiments, the tubular member and the thread may be integrally formed, for example, by a single mold. According to some embodiments, the thread may be formed as a separate element molded on, attached to or otherwise positioned on the tubular member. According to some embodiments, the tubular member and the thread may be made from a same or a different material. The tubular member and the thread may, according to some embodiments, be collectively referred to and/or resemble as a "screw" or an "Archimedes screw".

According to some embodiments, the tubular member may have a length of 5-15 cm, 6-10 cm, 7.5-10 cm or any other length within the range of 5-15 cm. Each possibility is a separate embodiment. According to some embodiments, the tubular member may have an outer diameter in the range of 2-10 mm, 2-5 mm, 3-4 mm or any other suitable diameter within the range of 2-10 mm. Each possibility is a separate embodiment. According to some embodiments, the tubular member may have an inner diameter in the range of 1-9 mm, 1-4 mm, 2-3 mm or any other suitable diameter within the range of 1-9 mm. Each possibility is a separate embodiment.

As used herein the terms "thread" and "screw thread" may be used interchangeably and may refer to a ridge formed on the outer surface of the tubular member.

According to some embodiments, the thread may be configured to penetrate the pericardium by being screwed through and/or by lifting the layers forming the pericardium. According to some embodiments, the penetration into the pericardial space is performed horizontally, i.e. along an axis essentially perpendicular to the axis pointing towards the heart/myocardium and to the longitudinal axis of the tubular member. According to some embodiments, as used herein, the terms "horizontally" and "essentially horizontally" with regards to the angle of penetration of the thread into the pericardial space may refer to an angle of 70°-120°, 80°-110°, or 85°-100° relative to the longitudinal axis of the tubular member. Each possibility is a separate embodiment.

According to some embodiments, the thread may be formed around the outer surface of the tubular member in a helical pattern. According to some embodiments, the thread may extend around the tubular member at least once, at least twice or at least three times. Each possibility is a separate embodiment.

According to some embodiments, the thread may be configured to secure and/or fasten the tubular member to the pericardium, thereby allowing medical instruments and/or medicaments to be delivered into the pericardial space and/or to the heart/myocardium, once access into the pericardial space has been gained.

According to some embodiments, the thread may be a sharpened thread configured to saw and/or cut through the pericardial layers. According to some embodiments, the thread may be a helical blade formed around the outer surface of the tubular member. According to some embodiments, the thread may be formed as an essentially horizontal ring around the outer surface of the tubular member.

According to some embodiments, the distal end of the thread may be essentially perpendicular to the longitudinal axis of the tubular member. According to some embodiments, the distal end of the thread may include a sharpened tip configured to puncture and/or cut at least one layer of the pericardium.

According to some embodiments, the treaded portion of the tubular member may have a length of 10 mm or less, 7 mm or less or 5 mm or less. Each possibility is a separate embodiment. According to some embodiments, the threaded portion may be positioned at a distal end of the tubular member. According to some embodiments, the distal most part of the thread may be positioned 0.5 mm-20 mm, 0.5-10 mm, 1-8 mm, 1-5 mm or any other suitable distance or range of distances within the range of 0.5-20 mm from the tubular member's end face. Each possibility is a separate embodiment. According to some embodiments, the tubular member may be threaded along its entire length. Alternatively, the tubular member may be threaded along part of its length, such as half of its length or less, a third of its length or less, a fifth of its length or less or a tenth of its length or less. Each possibility is a separate embodiment.

According to some embodiments, the thread comprises at least two, at least three or at least four threads. Each possibility is a separate embodiment.

As used herein, the term "atraumatic distal end" may refer to the end face of the tubular member being non-sharp so as to prevent it from damaging the heart and/or myocardium during penetration and/or when penetrated into the pericardial space.

According to some embodiments, the atraumatic distal end may be open ended. According to some embodiments, the end-face may be essentially flat. According to some embodiments, the end-face may be concave and/or rounded. According to some embodiments, the atraumatic tip may include a penetrable cover (also referred to herein as an "end cap") covering the end opening of the tubular member. According to some embodiments, the end face and/or penetrable cover may include a soft/and or elastic material configured to further protect the heart and/or myocardium from being damaged if encountered therewith.

According to some embodiments, the penetrable cover may include two, three, four or more flaps configured to cover the opening, for example, during advancement and penetration of the pericardium while allowing delivery of medical instruments or other tools, for example, after access into the pericardial space has been gained. According to some embodiments, the penetrable cover may be penetrable from within the lumen only. This may advantageously ensure that medical instruments may be delivered to the pericardial space from within the lumen while fat, facia or other materials are prevented from blocking the tubular member and/or from traveling retrograde into the lumen thereof, for example, during advancement of the tubular member toward the pericardium.

According to some embodiments, the device may include at least one sensor configured to detect penetration of the device into the pericardial space. According to some embodiments, the at least one sensor may be positioned on the end face of the device, on a distal end of the device, on the penetrable cover and/or on the thread. As a non-limiting example, the device may include a first sensor positioned on the end face and/or the penetrable cover and a second sensor positioned at a distal portion of the thread. According to some embodiments, the at least one sensor may be configured to monitor the entire procedure. Alternatively, the at least one sensor may be activated when the tubular member approaches and/or engages the pericardium. According to some embodiments, the at least one sensor may be activated along with activation of the rotation of the tubular member.

According to some embodiments, the at least one sensor may be a bio-impedance sensor configured to detect a change in impedance, conductivity, resistance or any other suitable electrical parameter as a result of penetration of the tubular member and/or the thread (or at least the distal part thereof) into the pericardial space and/or as a result of it being immersed in pericardial fluid. Each possibility is a separate embodiment.

Additionally or alternatively, the at least one sensor may be a liquid sensor configured to detect that the tubular member and/or the thread (or at least the distal part thereof) has entered a liquid environment, i.e. that entry into the pericardial space including the pericardial fluid has been attained.

Additionally or alternatively, the at least one sensor may be a pressure sensor configured to detect a change in pressure resulting from penetration of the tubular member and/or the thread (or at least the distal part thereof) into the pericardial space. Non-limiting examples of suitable pressure sensors include capacitive pressure sensors, electromagnetic pressure sensors, piezoelectric pressure sensors, resonant pressure sensors, and any other suitable pressure sensors. Each possibility is a separate embodiment.

Additionally or alternatively, the sensor may be a passive sensor such as an echogenic marker, a radiopaque marker or the like, configured to allow monitoring of the movement of the tubular member and/or the thread by imaging, such as, but not limited to, fluoroscopy, ultrasound, X-ray, IR etc. Each possibility is a separate embodiment.

According to some embodiments, the device may further include one or more sensors configured to detect an approaching of the device to the subject's heart and/or one or more sensors configured to detect systole. According to some embodiments, such sensor may further assist in preventing damage being caused to the heart. Additionally, detecting systole may allow synchronization of the rotation and/or progression of the tubular member and/or of the cutting, puncturing and/or penetration of the tubular member with the contraction phase of the cardiac cycle. According to some embodiments, the one or more sensors configured to detect an approaching of the device to the subject's heart and/or to detect systole may be the same sensor used for detecting penetration of the device into the pericardial space or a different sensor. According to some embodiments, the one or more sensors configured to detect an approaching of the device to the subject's heart and/or to detect systole may be a pressure sensor, a heart rate sensor, an impedance sensor, a PPG sensor or any other suitable sensor. Each possibility is a separate embodiment. Additionally or alternatively, the cardiac cycle may be monitored by ECG, in which case the rotation and/or progression of the tubular member may be synchronized to systole based on the ECG.

According to some embodiments, the proximal end of the tubular member may include an attachment element configured to attach the tubular member to a handle in such manner that detachment of the tubular member during use is prevented, as further described herein. According to some embodiments, the attachment element may be configured to be broken and/or otherwise disabled after a first use, so as to prevent unintended and hazardous reuse thereof.

According to some embodiments, the proximal end of the tubular member may include an activating element configured to verify proper connection of the tubular member to the handle. Non-limiting suitable activating elements include optical elements, conductive elements, bulges or other suitable elements configured to communicate and/or pair with matching elements and or matching detectors within the handle, as further elaborated hereinbelow.

According to some embodiments, the tubular member is configured for rotation and/or longitudinal movement when attached to a handle. According to some embodiments, rotation of the tubular member without advancement may cause the layers of the parietal pericardium to be lifted and/or separated, thereby facilitating the creation of a suitable workspace.

According to some embodiments, the tubular member may include more than one lumen, such as two, three, or more lumens. Each possibility is a separate embodiment. According to some embodiments, the more than one lumen may facilitate simultaneous insertion of more than one medical device and/or medicament.

According to some embodiments, there is provided a system for accessing a pericardial space of a subject in need thereof, the system comprising the device comprising a tubular member and a thread on an outer surface of the tubular member, as essentially described in embodiments herein, and a handle comprising a socket configured to receive the proximal end of the tubular member.

As used herein, the term "handle" may refer to any element configured to be grasped by a user (e.g. a physician) and to enable steering and or controlling the operation of the tubular member.

According to some embodiments, the handle may include a main body having a same longitudinal axis as the tubular member, when the tubular member is inserted into the socket. According to some embodiments, the handle may further include a grip configured to allow the handle to be comfortably grasped by the user and/or configured to be attached to or grasped by a robot performing the procedure. According to some embodiments, the grip may be perpendicular to the main body.

According to some embodiments, the handle may further include a first mechanism configured to rotate the device along its longitudinal axis, when the proximal end is inserted into the socket. According to some embodiments, the handle may further include a second mechanism configured to allow movement of the tubular member relative to the main body, such as but not limited to longitudinal and/or horizontal movement. According to some embodiments, the first and second mechanisms may be the same or different. According to some embodiments, the first and/or second mechanisms may be user controlled. Additionally or alternatively, the first and/or second mechanisms may be controlled by signals obtained from the one or more sensors. As a non-limiting example, the handle may enable operational control by a user who may activate the rotation and/or progressive movement of the tubular member, yet this operation may be overruled if the one or more sensors provides a signal indicative of penetration into the pericardial space and/or a signal indicative of a potentially hazardous proximity to the subject's heart. As another non-limiting example, the rotation and/or progression may be activated by a user, while the speed of rotation and/or progression and/or the length/duration of rotation and/or progression may be controlled based on signals obtained from the one or more sensors. As another non-limiting example, the rotation and/or progression may be determined according to medical characteristics of the patient, such as, but not limited to, the thickness of the pericardium or layers thereof, the amount of fluid in the pericardial space, or any other suitable medical characteristics or combination of characteristics. As another non-limiting example, the rotation and/or progression may be adjusted according to patient characteristics such as age, weight, gender, medical history, life style, or any other suitable patient characteristics or combination of characteristics.

According to some embodiments, the rotation and/or progression may be set manually or automatically, for example, based on input (e.g. medical and/or patient characteristics) entered through a user interphase.

According to some embodiments, the handle may include one or more control buttons, such as, but not limited to, a press button, or a trigger, for example at the grip section thereof, configured to enable user initiated control of the tubular member.

According to some embodiments, the one or more buttons may include a first button, or a first button position, which, when activated, initiates longitudinal advancing (and optionally axial motion) of the tubular member (without rotation), for example, as long as the button is pressed upon and/or until arrival to the superior fibrotic layer of the parietal pericardium and/or until the distal end/end face of the tubular member engages and/or reaches the pericardium. According to some embodiments, the speed of longitudinal advancement may be changed (e.g. reduced) as the tubular member approaches the pericardium, as, for example, determined based on a signal obtained from one or more sensors indicative thereof.

According to some embodiments, the one or more button, may be a trigger configured to control the rotation and/or longitudinal and/or axial movement of the tubular member, for example, depending on the pressure applied on the trigger.

According to some embodiments, the one or more buttons may include a second button, or a second button position, which, when activated, initiates rotation of the tubular member, and optionally a third button or a third button position, which, when activated, initiates rotation simultaneously with longitudinal advancement of the tubular member. These buttons or button positions may be selectively activated during the penetration of the tubular member into the pericardial space. According to some embodiments, the rotating of the tubular member concurrently with longitudinal advancement may be configured to screw the tubular member through and/or into the layers of the parietal pericardium. According to some embodiments, the rotation of the tube without advancement may cause the layers of the parietal pericardium to be lifted and/or separated, thereby facilitating the creation of a suitable workspace.

According to some embodiments, the operation of the device may be semi- or fully automatic rather than or in addition to user guided operation. According to some embodiments, the handle includes a control circuit or components of a control circuit configured to obtain signals from the one or more sensors and/or through a user interphase and to control the rotation, and/or longitudinal, and/or axial movement of the tubular member in response thereto. It is understood that such automatic or semiautomatic operational control may enable carrying out the procedure using a robot.

According to some embodiments, the socket may include a locking mechanism configured to lock the tubular member once properly inserted into the socket. According to some embodiments, the handle may include an eject mechanism configured to release the tubular member from the socket, for example, after completion of the procedure. For safety reasons, the eject mechanism may be prevented from being activated during the procedure. According to some embodiments, the eject mechanism may break or otherwise disable an attachment element positioned on the tubular member, thereby preventing reuse thereof.

According to some embodiments, the socket may include a verification element configured to prevent activation of the device prior to verification of proper insertion/connection/attachment of a tubular member within the socket, for example, by communication and/or paring between the activating element of the tubular member and the verification element of the socket. As a non-limiting example, the socket may include an open electrical circuit, which may be closed by a tubular member comprising a conductive element when inserted into the socket. According to some embodiments, the verification element and/or the eject mechanism may be configured to break or otherwise disable the activating element of the tubular member upon ejection of the tubular member from the socket, thereby preventing reuse thereof.

According to some embodiments, the system may further include a display. According to some embodiments, the display may be positioned on the handle. Additionally or alternatively, the display may be a separate element, functionally connected to the system.

According to some embodiments, the display may include at least one indicator, such as, but not limited to, three or more color lamps, configured to provide and/or display real-time guidance and/or monitoring of the procedure.

According to some embodiments, the indicator may be a visual indicator. As a non-limiting example, differently colored light may be indicative of different steps of the procedure. For example, a blue light may be indicative of the device advancing through tissues on its way to the heart, yellow light indicative of reaching the outer layer of the pericardium, a green light indicative of accomplishment of the penetration into the pericardial space and a red light indicative of a problem encountered during the procedure. It is understood that the colors set forth are illustrative only and that different colors may also be utilized. It is further understood that each color indicator may be displayed by a dedicated display (i.e. a specific lamp). According to some embodiments, the indicator may alternatively or additionally include an audial indicator indicative of the step of the procedure, of accomplishment of the procedure (i.e. penetration into the pericardial space) and/or indicative of a problem encountered during the procedure.

According to some embodiments, the display may be configured to display values obtained from the one or more sensors (e.g. values obtained from the bio-impedance sensor).

According to some embodiments, the handle and/or a processing unit functionally connected thereto may further include a data storage unit configured to store data, such as data obtained from the one or more sensors for future reference. Such data may, for example, enable detecting correlations between the procedure parameters (e.g. duration of the procedure, bio-impedance values, etc.) with the outcome of the procedure.

According to some embodiments, there is provided a method for accessing a pericardial space of a subject in need thereof, the method including inserting a device into a chest cavity, for example, through a subxiphoid incision or through the thorax, the device including a tubular member having an atraumatic distal end and a thread formed on, and at least partially around, an outer surface of the tubular member, proximal to the distal end; advancing the device to the pericardium until the atraumatic distal end reaches, touches and/or presses against the pericardium; and rotating the tubular member along its longitudinal axis, such that the thread cuts, punctures and/or penetrates the pericardium, thereby allowing the tubular member's distal end to penetrate into the pericardial space.

According to some embodiments, the method may be minimally invasive.

According to some embodiments, the pressing of the tubular member against the pericardium, such as the parietal pericardium, may cause the outer layer of the pericardium—the fibrous pericardium—to fold around the thread, thereby facilitating its essentially horizontal penetration.

According to some embodiments, the rotating of the tubular member may include rotation of the tubular member concurrent with its longitudinal advancement. According to some embodiments, the concurrent rotation and longitudinal advancement of the tubular member may screw the thread into the layers forming the pericardium, thereby securing the tubular member thereto.

According to some embodiments, the rotating of the tubular member may include rotation of the tubular member in the absence of longitudinal advancement. According to some embodiments, such rotation without advancement may cause the layers forming the parietal pericardium to be lifted and/or separated.

According to some embodiments, rotation of the tubular member may generate a torque which brings about penetration into the pericardium.

According to some embodiments, the method further comprises obtaining one or more signals from one or more sensors, such as, but not limited to, one or more bio-impedance sensors configured to detect penetration of the device into the pericardial space.

According to some embodiments, the method further comprises obtaining one or more signals from one or more sensors, such as, but not limited to, one or more pressure sensors configured to detect arrival/approaching of the tubular member to the pericardium.

According to some embodiments, the method may further include displaying an indication of the procedure's progress.

According to some embodiments, the method may further include displaying the signals obtained from the one or more sensors.

According to some embodiments, the method may further include halting, pausing and/or terminating the rotation and/or advancement of the tubular member when a signal indicating that penetration into the pericardial space has been accomplished.

According to some embodiments, the method may further include inserting a medical instrument through the tubular member's lumen into the pericardial space, once penetration has been accomplished. According to some embodiments, the method may further include delivering a medicament through the tubular member's lumen to the pericardial space, once penetration has been accomplished.

Figure 1A:
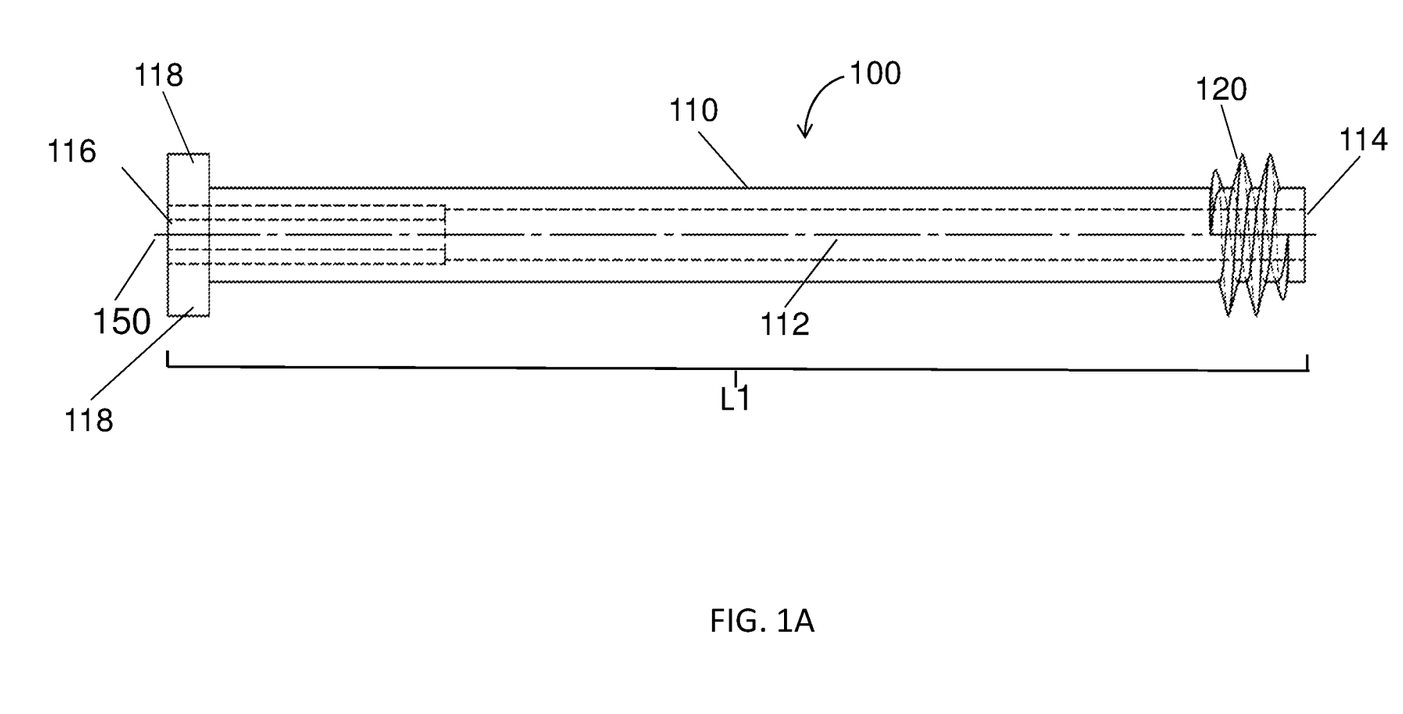
FIG. 1A schematically illustrates an exposed side view of a device for accessing a pericardial space comprising a tubular member forming a lumen, the tubular member having an atraumatic distal end and a thread formed on its outer surface, according to some embodiments.
Figure 1B:
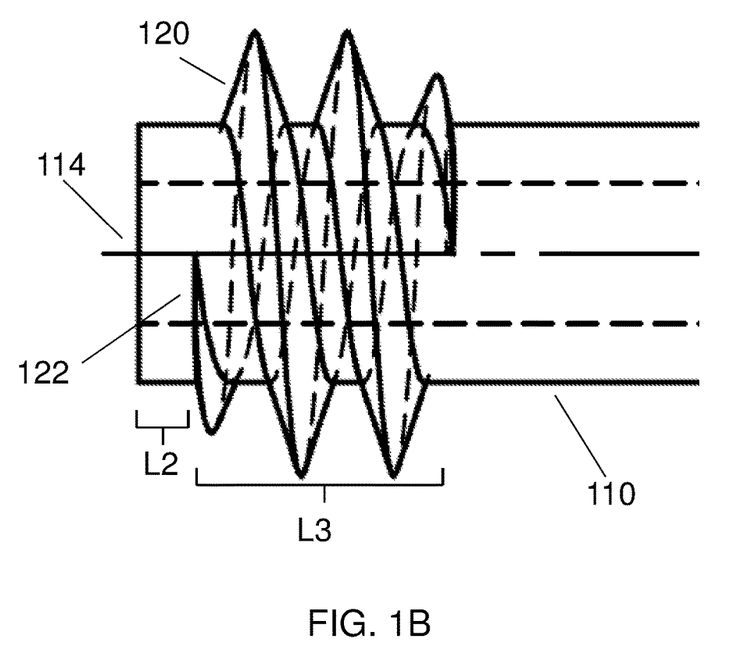
FIG. 1B schematically illustrates a side view of a distal part of the device for accessing a pericardial space shown in FIG. 1A.
Figure 1C:
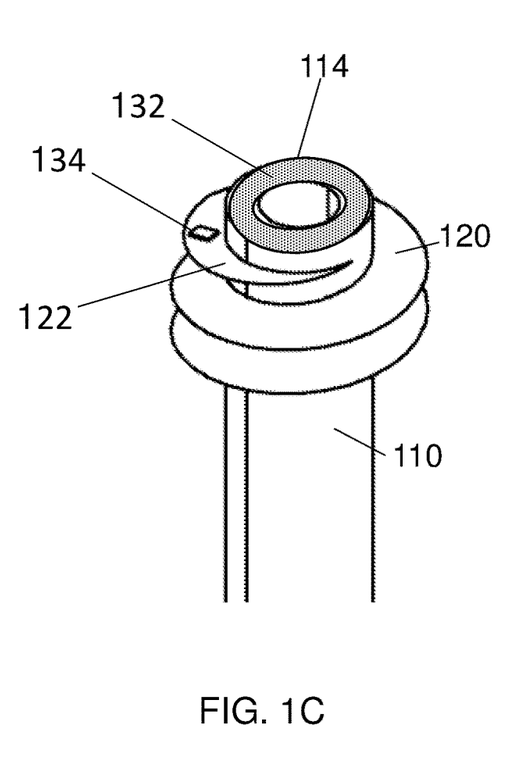
FIG. 1C schematically illustrates a top perspective view of a distal part of the device for accessing a pericardial space shown in FIG. 1A.

Reference is now made to FIG. 1A-FIG. 1C, which schematically illustrates a side view of a device 100 for accessing a pericardial space (not shown) according to some embodiments. Device 100 includes a tubular member 110 having a length L1 of about 5-15 cm, e.g. 10 cm. Tubular member 110 has a lumen 112 sized and shaped to allow passage therethrough of medical instruments and/or medicaments. Tubular member 110 further includes an atraumatic distal end 114 (also referred to herein as an "end face"), which may be flat or rounded (option not shown) and which may be open ended or covered by an end cap, such as end cap 300 of FIG. 3 (option not shown). According to some embodiments, distal end 114 may further include a soft material, as essentially described herein. Tubular member 110 further includes a thread 120 formed on its outer surface thus resembling an Archimedes screw. Thread 120 is formed at a distance L2 of about 2-10 mm proximally to distal end 114 (e.g. 5 mm), so as to prevent thread 120 from cutting/harming tissue located distally to distal end 114. Thread 120 is configured to cut, puncture and/or penetrate a pericardium (not shown), when in use. According to some embodiments, thread 120 may be configured to penetrate the pericardium by being screwed through and/or by lifting the layers forming the pericardium, as essentially described herein. According to some embodiments, thread 120 penetrates the pericardial space essentially horizontally, i.e. along an axis essentially perpendicular to the axis pointing towards the heart/myocardium. According to some embodiments, thread 120 may be configured to secure and/or fasten tubular member 110 to the pericardium, thereby allowing medical instruments and/or medicaments to be delivered into the pericardial space and/or to the heart/myocardium, once access into the pericardial space has been gained, as essentially described herein. Thread 120 may be sharp so as to facilitate it being sawed into and/or cut through the pericardial layers. According to some embodiments, a distal end 122 of thread 120 may be essentially perpendicular to the longitudinal axis 150 of tubular member 110. According to some embodiments, distal end 122 of thread 120 may include a sharpened tip configured to puncture and/or cut at least one layer of the pericardium. According to some embodiments, the threaded portion of tubular member 110 may have a length L3 of, for example, 10 mm or less. Device 100 further includes at least one sensor configured to detect penetration of the device into the pericardial space, here bio-impedance sensor 132 positioned on distal end 114 of tubular member 110 and bio-impedance sensor 134 positioned on distal end 122 of thread 120. Bio-impedance sensor 132 is here shown to be ring shaped and to cover the entire end face of distal end 114; however, other configurations and shapes are also applicable and within the scope of this disclosure. Similarly, bio-impedance sensor 134 is here shown to be positioned on distal end 122 of thread 120, however other configurations, such as along the entire length of thread 120 are also applicable and thus within the scope of this disclosure. According to some embodiments, bio-impedance sensor 132 and/or bio-impedance sensor 134 may be configured to monitor during the entire procedure or selectively when tubular member 110 approaches and/or engages the pericardium and/or when rotation of tubular member 110 is initiated. According to some embodiments, device 100 may further include one or more sensors, such as a pressure sensor (not shown) configured to detect an approaching of the device to the subject's heart and/or to detect systole, as essentially described herein. Proximal end 116 of tubular member 110 may include an attachment element 118, such as bulges configured for attachment of tubular member 110 to a handle (such as handle 250 in FIG. 2) in such manner that detachment of tubular member 110 during use is prevented, as described herein. According to some embodiments, attachment element 118 may be configured to be broken and/or otherwise disabled after a first use, so as to prevent unintended and hazardous reuse thereof. According to some embodiments, proximal end 116 of tubular member 110 may include an activating element (not shown) configured to verify proper connection of tubular member 110 to the handle, as essentially described herein.

Figure 2:
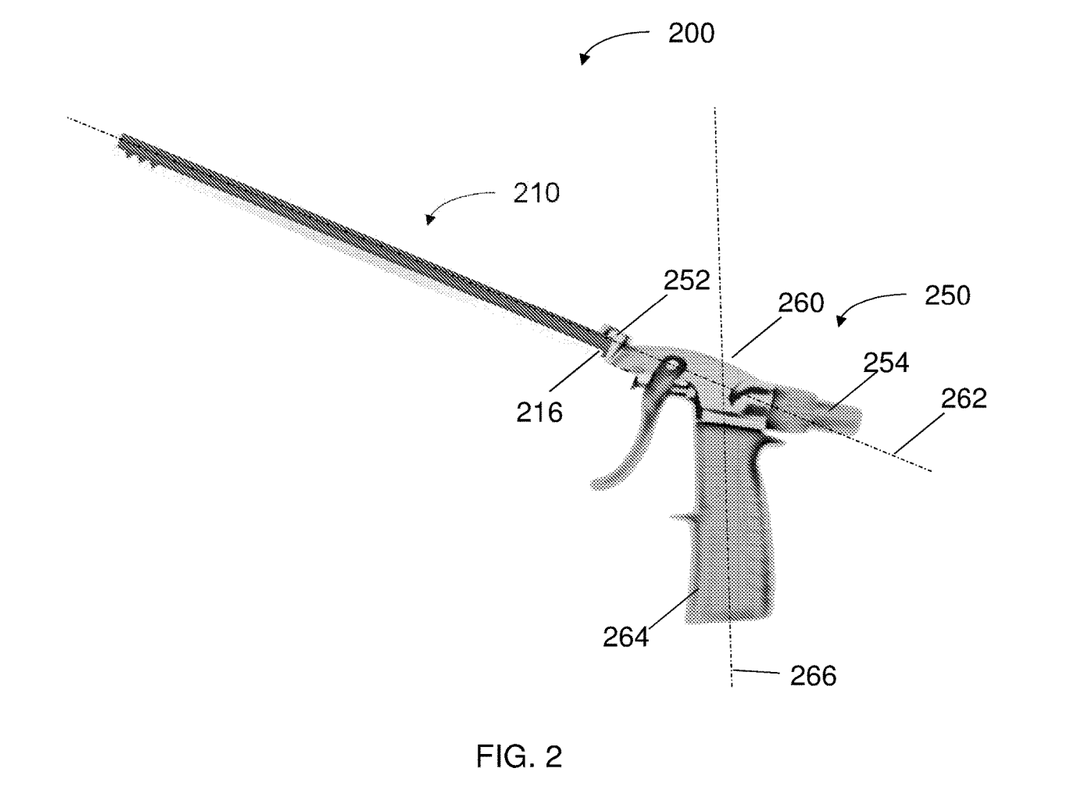
FIG. 2 schematically illustrates a system for accessing a pericardial space comprising a tubular member such as the tubular member of FIG. 1 inserted into the socket of a handle, according to some embodiments.

Reference is now made to FIG. 2, which schematically illustrates a system 200 for accessing a pericardial space (not shown). System 200 includes a tubular member 210, similar to tubular member 110 of FIG. 1, and a handle 250 comprising a socket 252 into which proximal end 216 of tubular member 210 is inserted. Handle 250 includes a main body 260 having a same longitudinal axis 262 as tubular member 210. Handle 250 further includes a grip 264 configured to allow handle 250 to be comfortably grasped by a user and/or configured to be attached to or grasped by a robot performing the procedure. Grip 264 is here shown to have a longitudinal axis 266 essentially perpendicular to longitudinal axis 262 of main body 260; however, other configurations may also be envisaged and are within the scope of this disclosure. According to some embodiments, handle 250 may include a mechanism (not shown) configured to rotate tubular member 210 along longitudinal axis 262, as essentially described herein. According to some embodiments, handle 250 may further include a second mechanism (not shown) configured to allow longitudinal (i.e. along longitudinal axis 262) and optionally axial (i.e. perpendicularly to longitudinal axis 262) movement of tubular member 210 relative to main body 260. According to some embodiments, the first and/or second mechanisms may be user controlled and/or controlled by signals obtained from one or more sensors, such as bio-impedance sensors 132 and 134 (shown in FIG. 1A-FIG. 1C), as essentially described herein. According to some embodiments, handle 250 may include one or more control buttons (not shown), for example on grip 264, configured to enable user-initiated control of the rotation and/or movement of tubular member 210, as essentially described herein. Socket 252 may optionally include a locking mechanism (not shown) configured to lock tubular member 210 upon its insertion therein. According to some embodiments, handle 250 may also include an eject mechanism 254 configured to release tubular member 210 from socket 252, for example, after completion of the procedure. For safety reasons, eject mechanism 254 may be prevented from being activated during the procedure. Optionally, eject mechanism 254 may break or otherwise disable the locking mechanism on tubular member 210, thereby preventing reuse thereof. Optionally, socket 252 further includes a verification element (not shown) configured to prevent activation of system 200 prior to verification of proper insertion/connection/attachment of tubular member 210 within socket 252, for example, by communication and/or paring between an activating element positioned on tubular member 210 and the verification element of socket 252, as essentially described herein. According to some embodiments, system 200 may further include a display (not shown) configured to display an indication as to the advancement of the procedure and/or values obtained from the one or more sensors, as essentially described herein.

Figure 3:
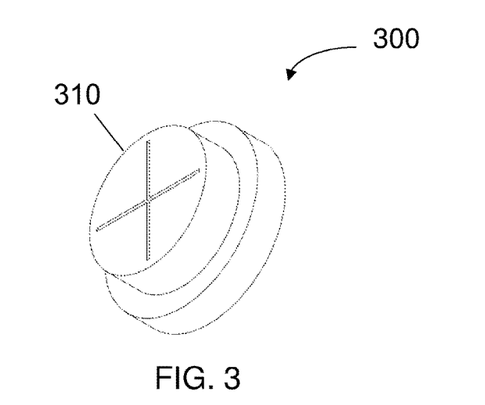
FIG. 3 schematically illustrates a penetrable end cap configured to cover the end opening of a tubular member, such as the tubular member of FIG. 1, according to some embodiments.

Reference is now made to FIG. 3, which schematically illustrates a penetrable end cap 300 configured to cover distal end 116 of tubular member 110, according to some embodiments. Penetrable end cap 300 may include flaps 310 configured to cover the opening of lumen 112, for example, during advancement and/or penetration of tubular member 110 into the pericardium, while allowing delivery of medical instruments or medicaments (not shown) therethrough. According to some embodiments, penetrable end cap 300 may be penetrable from within lumen 112 only. This may advantageously ensure that medical instruments can be delivered to the pericardial space from within the lumen while fat, facia or other materials are prevented from blocking the tubular member and/or from traveling retrograde into the lumen thereof, for example, during advancement of the tubular member toward the pericardium. It is understood that in embodiments where tubular member 110 is covered by end cap 300, bio-impedance sensor 132 may be positioned on penetrable cap 300 (configuration not shown) rather than on the end face of tubular member 110 as shown in FIG. 1.

Figure 4:
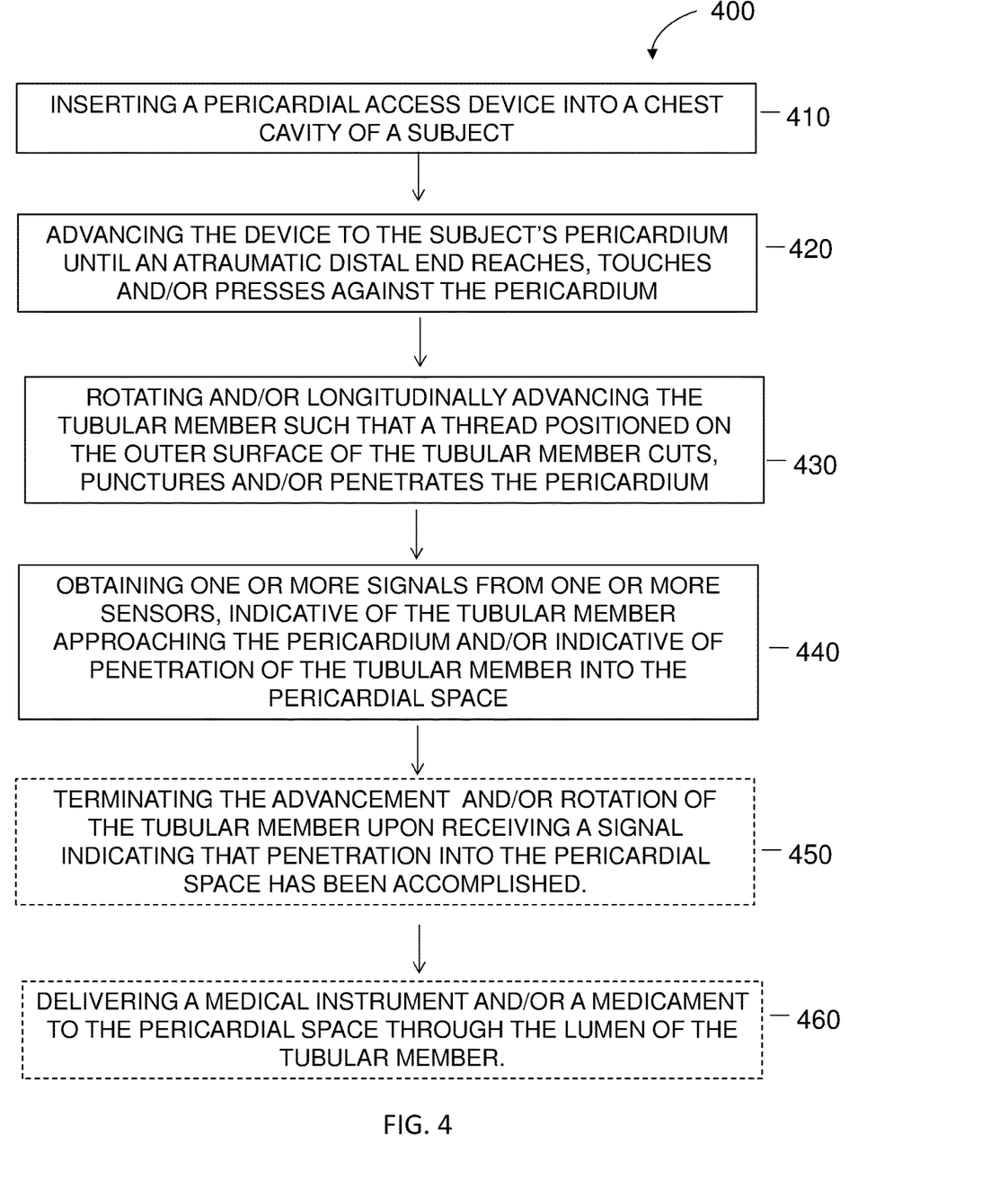
FIG. 4, is an illustrative flow chart of a method for accessing a pericardial space, according to some embodiments.

Reference is now made to FIG. 4, which is an illustrative flowchart of a method 400 for accessing a pericardial space, according to some embodiments. In step 410 of the method, a pericardial access device, such as the device of FIG. 1A, is inserted into a subject's chest cavity, the device including a tubular member having an atraumatic distal end and a thread formed on, and at least partially around, an outer surface of the tubular member, proximal to the distal end, as essentially described herein. In step 420 the device is advanced toward the pericardium until the atraumatic distal end of the device reaches, touches and/or presses against the pericardium, such that the fibrotic pericardial layer folds around the thread of the tubular member. In step 430 the tubular member is rotated and/or advanced along its longitudinal axis, such that the thread cuts, punctures and/or penetrates the pericardium. According to some embodiments, step 430 may include initially rotating the tubular member, while concurrently advancing the tubular member along its longitudinal axis, thereby causing the thread to puncture, pierce and/or screw into the pericardium layers. According to some embodiments, step 430 may further include rotating the tubular member in the absence of longitudinal advancement, thereby causing the layers of the pericardium to be lifted and/or separated. According to some embodiments, the method may further include step 440 in which one or more signals from one or more sensors, such as, but not limited to, one or more pressure sensors and/or one or more bio-impedance sensors are obtained, the signals being indicative of the tubular member approaching the pericardium and/or the tubular member penetrating into the pericardial space. Optionally, the method may further include a step 450 of terminating the advancement and/or rotation of the tubular member once a signal indicating that penetration into the pericardial space has been accomplished and/or completed, has been obtained. Optionally, the method may further include a step 460 in which a medical instrument and/or a medicament is delivered to the pericardial space through the lumen of the tubular member.

It is understood that the some of the steps set forth may be consecutive while others may be executed simultaneously. For example, the device is first inserted into the chest cavity and only thereafter advanced toward the pericardium. For example, the signals may be obtained during the entire procedure or parts thereof and not as a final step, as indicated in the flowchart.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising", when used in this specification, specify the presence of stated features, integers, steps, operations, elements, or components, but do not preclude or rule out the presence or addition of one or more other features, integers, steps, operations, elements, components, or groups thereof. According to some embodiments, the term "comprising" may be replaced by the term "consisting essentially of" or "consisting of".

The invention may be described in the general context of computer-executable instructions, such as program modules, being executed by a computer. Generally, program modules include routines, programs, objects, components, data structures, and so forth, which perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. A device for accessing a pericardial space of a subject in need thereof, the device comprising:
    a tubular member having an open ended atraumatic distal end, a proximal end, and a wall having an outer surface and an inner surface forming a lumen, wherein the tubular member and the atraumatic distal end are not movable with respect to each other;
    a thread formed on, and at least partially around, said outer surface, proximal to said atraumatic distal end, wherein said thread ends at a sharp distal tip spaced at a constant distance of between 2 and 10 mm, inclusive, from the atraumatic distal end,
    a first bio-impedance sensor positioned on the atraumatic distal end; and
    a second bio-impedance sensor positioned on a distal end of the thread;
    wherein said thread is configured to cut, puncture and/or penetrate a pericardium, when in use, at an essentially perpendicular and/or tangential angle relative to said longitudinal axis of said tubular member, and
    wherein the atraumatic distal end is configured to protect said subject's heart and/or myocardium from being damaged.

2. The device according to claim 1, wherein the proximal end of said tubular member comprises an attachment mechanism configured to reversibly attach said tubular member to a handle.

3. The device according to claim 2, wherein the proximal end of said tubular member comprises a securing element configured to ensure proper connection of said tubular member to said handle.

4. The device according to claim 1, wherein said tubular member is open ended, thereby enabling passing a medical instrument and/or medicament through said lumen into said pericardial space, when said device has penetrated into said pericardial space.

5. The device according to claim 1, wherein said tubular member comprises a penetrable end-cap covering the lumen opening; wherein said penetrable end-cap is penetrable from within said lumen, such that a medical instrument and/or medicament passed through said lumen can enter said pericardial space.

6. A method for accessing a pericardial space of a subject in need thereof, the method comprising:
    inserting the device of claim 1 into a chest cavity;
    advancing the device to the pericardium until said atraumatic distal end reaches and/or presses against said pericardium; and
    rotating said tubular member along its longitudinal axis, such that said thread cuts, punctures and/or penetrates said pericardium, thereby allowing said tubular member's distal end to enter said pericardial space.

7. The method according to claim 6, further comprising moving said tubular member along its longitudinal and/or axial axis concurrently with the rotating thereof, thereby screwing said thread through and/or into said pericardium.

8. The method according to claim 7, further comprising rotating said tubular member without advancement, thereby lifting and/or separating layers of the pericardium.

9. The method according to claim 8, further comprising generating a workspace by rotating said tubular member without advancement, thereby lifting and/or separating layers of the pericardium.

10. The method according to claim 9, wherein the device further comprises one or more sensors configured to detect penetration of said device into said pericardial space and wherein the method further comprising obtaining a signal from the one or more sensors.

11. The method according to claim 10, wherein, when a signal indicative of penetration into said pericardial space is obtained, said rotation and/or longitudinal movement of said tubular member is halted.

12. The method according to claim 11, further comprising inserting a medical instrument through said tubular member's lumen into said pericardial space.

13. The method according to claim 12, further comprising delivering a medicament through said tubular member's lumen to said pericardial space.

* * * * *